United States Patent (12) United States Patent
Toyama et al.

(10) Patent No.: US 12,090,268 B2
(45) Date of Patent: Sep. 17, 2024

(54) CONNECTION UNIT FOR AIR FEEDING TUBE, AND METHOD OF FEEDING AIR INTO CONNECTION UNIT FOR AIR FEEDING TUBE

(71) Applicant: OLYMPUS CORPORATION, Tokyo (JP)

(72) Inventors: Motoyasu Toyama, Hachioji (JP); Kunitoshi Hiraga, Tama (JP); Shinya Torii, Tokyo (JP); Koji Yamaoka, Hamura (JP); Takefumi Uesugi, Tachikawa (JP); Yuma Kasuya, Fuchu (JP); Keita Kimura, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 507 days.

(21) Appl. No.: 17/343,129

(22) Filed: Jun. 9, 2021

(65) Prior Publication Data
US 2021/0290865 A1   Sep. 23, 2021

Related U.S. Application Data (63) Continuation of application No. PCT/JP2018/045867, filed on Dec. 13, 2018.

(51) Int. Cl.
*A61M 39/12* (2006.01)
*A61M 13/00* (2006.01)
*A61M 39/02* (2006.01)

(52) U.S. Cl.
CPC .......... *A61M 13/003* (2013.01); *A61M 39/12* (2013.01); *A61M 2039/0279* (2013.01); *A61M 2210/1067* (2013.01)

(58) Field of Classification Search
CPC ................ A61M 13/003; A61M 39/12; A61M 2039/0279; A61M 2039/0282;
(Continued)

(56) References Cited

U.S. PATENT DOCUMENTS 2,266,705 A * 12/1941 Fox .................... A61M 11/06
128/200.22
2010/0089399 A1* 4/2010 Landis .............. A61M 16/0427
128/205.12

FOREIGN PATENT DOCUMENTS

JP       08-010216 A    1/1996
JP    2000-237126 A    9/2000
(Continued)

OTHER PUBLICATIONS

International Search Report dated Mar. 26, 2019 received in PCT/JP2018/045867.

*Primary Examiner* — Phillip A Gray
*Assistant Examiner* — Anna E Goldberg-Richmeier
(74) *Attorney, Agent, or Firm* — Scully, Scott, Murphy & Presser, P.C.

(57) ABSTRACT

A connection unit for air feeding tube is a connection unit to which an air feeding tube is connectable and fixable and which includes: a first pipe having an opening through which gas from the air feeding tube flows in; a second pipe that is configured to be arrangeable substantially parallel to a surface of a bed used in an examination, and includes an opening through which the gas flows out; and an air feeding flow path which is formed to include the two openings and through which the gas is fed. When the air feeding tube is fixed to the connection unit for air feeding tube and is used, a part of the air feeding flow path for the gas is formed so as to pass through an area located at a position opposite to a gravitational direction with respect to a central axis of the second pipe.

16 Claims, 8 Drawing Sheets (58) Field of Classification Search
CPC ...... A61M 2210/1067; A61M 16/0808; A61M 16/0816; A61M 39/00; A61M 39/10; A61M 16/08; A61M 16/047; A61M 16/0477; A61B 17/3423

See application file for complete search history.

(56) References Cited

FOREIGN PATENT DOCUMENTS

| | | |
|---|---|---|
| JP | 2005-176908 A | 7/2005 |
| JP | 2012-504030 A | 2/2012 |
| JP | 2012-231896 A | 11/2012 |

\* cited by examiner

CONNECTION UNIT FOR AIR FEEDING TUBE, AND METHOD OF FEEDING AIR INTO CONNECTION UNIT FOR AIR FEEDING TUBE

CROSS REFERENCE TO RELATED APPLICATION

This application is a continuation application of PCT/JP2018/045867 filed on Dec. 13, 2018, the entire contents of which are incorporated herein by this reference.

BACKGROUND OF THE INVENTION

1. Field of the Invention

The present invention relates to a connection unit for air feeding tube which is used in surgery and to which an air feeding tube is connected, and a method of feeding air into the connection unit for air feeding tube.

2. Description of the Related Art

In endoscopic surgery, a trocar is used when an instrument, such as a rigid endoscope, is inserted into a body cavity. During surgery, carbon dioxide gas is fed into the body cavity through the trocar to secure a surgical visual field for the rigid endoscope and secure a treatment space in the body cavity.

For example, also in transanal total mesorectal excision (hereinafter called TaTME), in order to secure the surgical visual field of the rigid endoscope and secure the treatment space, a rectum is inflated with carbon dioxide gas using an insufflation device, and treatment is performed. The insufflation device controls a pressure reducing valve and a flow rate regulation valve to adjust the carbon dioxide gas to a predetermined pressure and flow rate, and supplies the regulated carbon dioxide gas into the rectum.

Typically, in TaTME, a predetermined access port for expanding an anus and for allowing a rigid endoscope and a treatment instrument to be inserted, is arranged at the anus. A trocar is punctured through the access port, an air feeding tube is connected to the trocar, and carbon dioxide gas is supplied into the rectum.

In typical laparoscopic surgery, through water feeding for a treatment, such as cauterization of an affected site, and for irrigation, liquid, such as blood and normal saline, is accumulated in an abdominal cavity. However, in such typical laparoscopic surgery, the position of a trocar is higher than the position of the surface of the liquid. Accordingly, no liquid enters the inside of an air feeding tube.

SUMMARY OF THE INVENTION

A connection unit for air feeding tube according to an aspect of the present invention is a connection unit for air feeding tube to which an air feeding tube is connectable and fixable, the connection unit including: a first pipe that includes a first opening through which gas from the air feeding tube flows in; a second pipe that is configured to be arrangeable substantially parallel to a surface of a bed used in an examination, and includes a second opening through which the gas flows out; and an air feeding flow path which is formed to include the first opening and the second opening and through which the gas is fed, wherein when the air feeding tube is fixed to the connection unit for air feeding tube and is used, a part of the air feeding flow path for the gas is formed so as to pass through an opposite side area located at a position opposite to a gravitational direction with respect to a central axis of the second pipe.

A method of feeding air into a connection unit for air feeding tube according to an aspect of the present invention is a method of feeding air into a connection unit for air feeding tube to which an air feeding tube is connectable and fixable, the method including: fixing the air feeding tube to the connection unit for air feeding tube to form an air feeding flow path for gas including a first opening of a first pipe and a second opening of a second pipe, a part of the air feeding flow path for the gas being formed so as to pass through an opposite side area located at a position opposite to a gravitational direction with respect to a central axis of the second pipe; allowing the gas from the air feeding tube to flow in through the first opening of the first pipe; and allowing the gas to flow out of the second opening of the second pipe arranged substantially parallel to a surface of a bed used in an examination.

DETAILED DESCRIPTION OF THE PREFERRED EMBODIMENTS

Hereinafter, embodiments of the present invention are described with reference to the drawings.

First Embodiment (Configuration of Surgical System)

Figure 1:
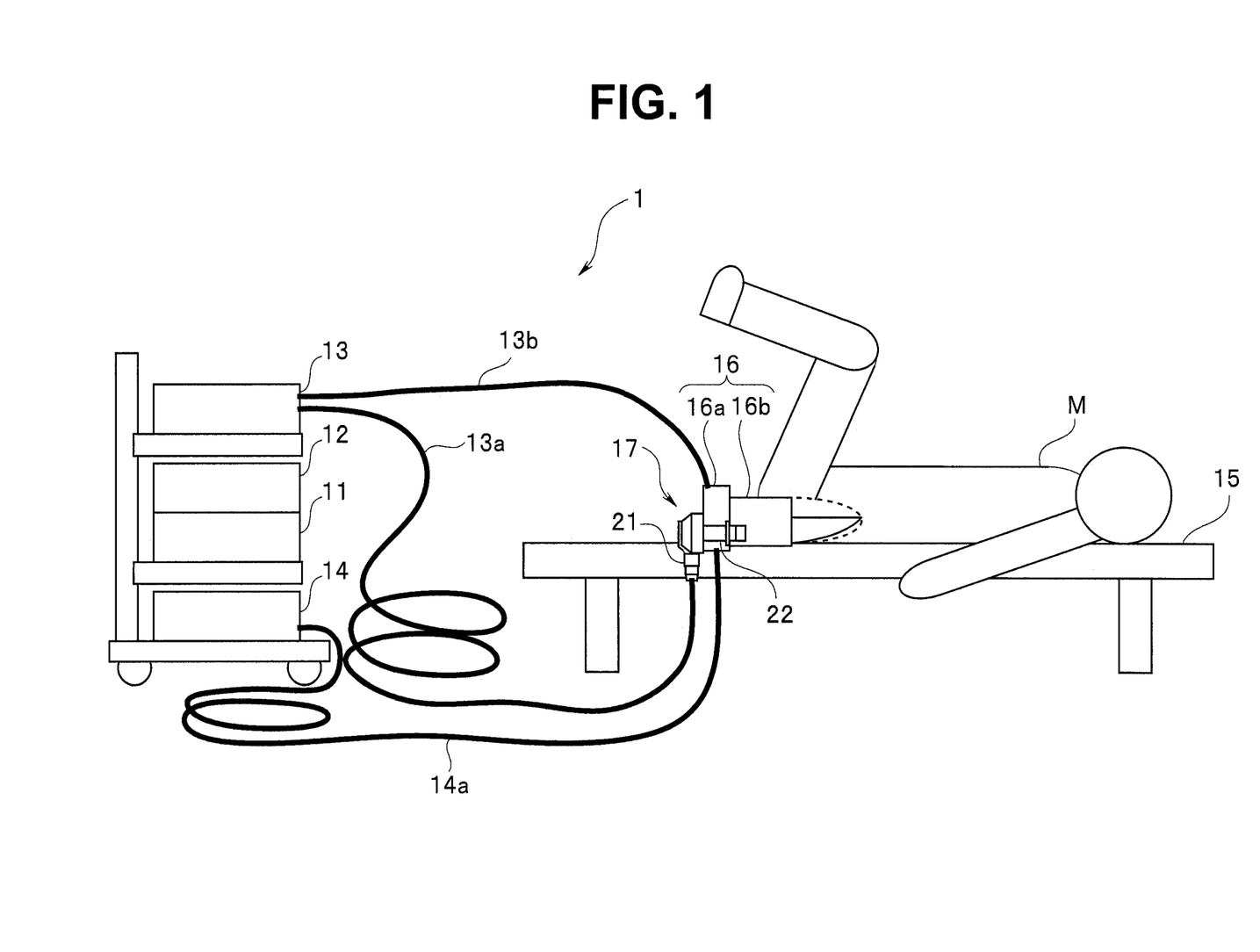
FIG. 1 is a schematic configuration diagram of a surgical system according to a first embodiment of the present invention.

FIG. 1 is a schematic configuration diagram of a surgical system according to a first embodiment. FIG. 1 shows an example of the surgical system when TaTME is performed. The surgical system 1 includes a video processor 11 for an endoscope, a light source device 12 for the endoscope, an insufflation device 13, and a suction device 14.

An endoscope, not shown, is connected to the video processor 11, and the video processor 11 generates an endoscope image obtained by the endoscope, and displays the image on a display device, not shown. The light source device 12 generates illumination light to be supplied to a light guide arranged in the endoscope. The illumination light generated by the light source device 12 is emitted through an illumination window at a distal end portion of the endoscope.

The insufflation device 13 feeds gas, such as carbon dioxide gas, into a body cavity of a patient. Accordingly, an end of an air feeding tube 13a is connected to the insufflation device 13. The other end of the air feeding tube 13a is connected to a connection unit 17 for air feeding tube, described later.

Furthermore, an end of an after-mentioned pressure measurement tube 13b for measuring the pressure in a rectum is connected to the insufflation device 13. The other end of the pressure measurement tube 13b is connected to a pressure measurement port of an after-mentioned access port 16. The suction device 14 performs suction of liquid in a body cavity of a patient M. Accordingly, an end of a suction tube 14a is connected to the suction device 14.

In a state where the patient M lies on a bed 15 in the supine position, a procedure of TaTME is performed. The access port 16 is attached to the anus of the patient M. The access port 16 is an access instrument for surgery, and includes a seal cap 16a, and an access channel portion 16b for allowing a treatment instrument or the like to be inserted into the rectum. The access channel portion 16b is inserted into the anus of the patient M.

The connection unit 17 for air feeding tube is attached to the access port 16. The seal cap 16a is a flexible member that includes a sealable access surface portion including a gel pad surface, and is for keeping the inside of the access channel portion 16b hermetic.

A plurality of trocar-type inlet port members (not shown) are attached to the seal cap 16a through the seal cap 16a. Each of instruments, such as a rigid endoscope and treatment instruments, are insertable into the rectum through the inlet port member.

The connection unit for air feeding tube (hereinafter, also simply called a connection unit) 17 is attached to the access surface portion of the seal cap 16a. The distal end portion of the air feeding tube 13a is connected to the connection unit 17 for air feeding tube.

Carbon dioxide gas fed from the insufflation device 13 to the air feeding tube 13a is supplied into the access port 16 through the connection unit 17 for air feeding tube. Since the access port 16 attached to the anus seals the inside of the rectum, the carbon dioxide gas inflates the rectum.

The access port 16 includes a pressure measurement port (not shown) to which the other end of the pressure measurement tube 13b described above is connected. The insufflation device 13 calculates an air feeding rate of carbon dioxide gas so as to keep the inside of the rectum to a predetermined pressure while the device monitors presence or absence of clogging or the like of the air feeding tube 13a on the basis of an estimated pressure in the rectum calculated from the air feeding rate to the air feeding tube 13a and of a detected pressure in the rectum detected through the pressure measurement port, and feeds carbon dioxide gas at the calculated air feeding rate into the air feeding tube 13a.

Since a predetermined space is secured in the rectum by maintaining the inside of the rectum to the predetermined pressure, a surgical visual field and a treatment space for a procedure are appropriately secured. As a result, a surgeon can perform a treatment with a treatment instrument while the surgeon views the inside of the rectum.

(Unit for Air Feeding Tube)

Figure 2:
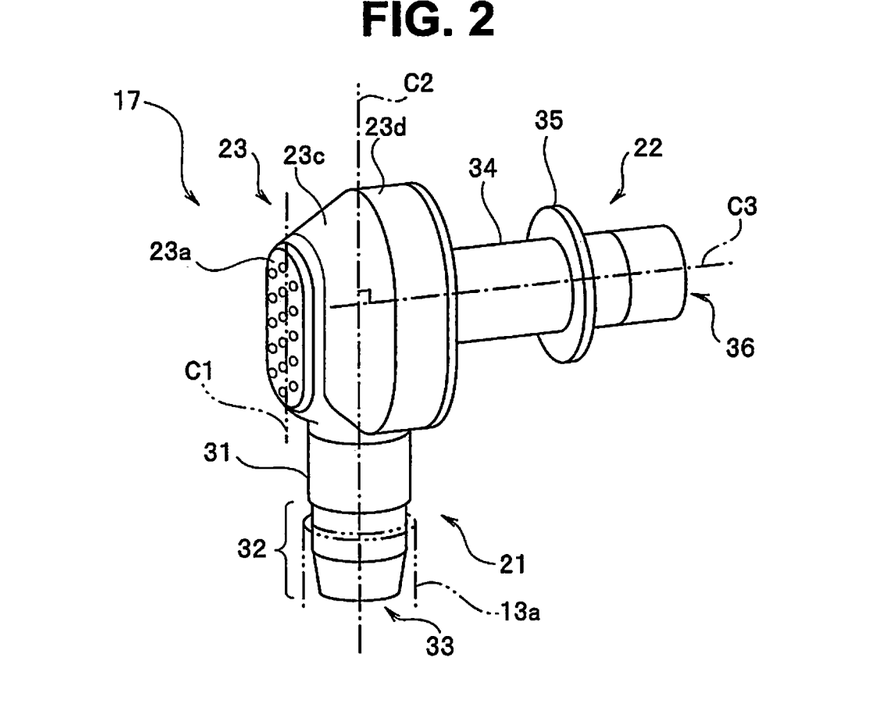
FIG. 2 is a perspective view of a connection unit for air feeding tube according to the first embodiment of the present invention.
Figure 3:
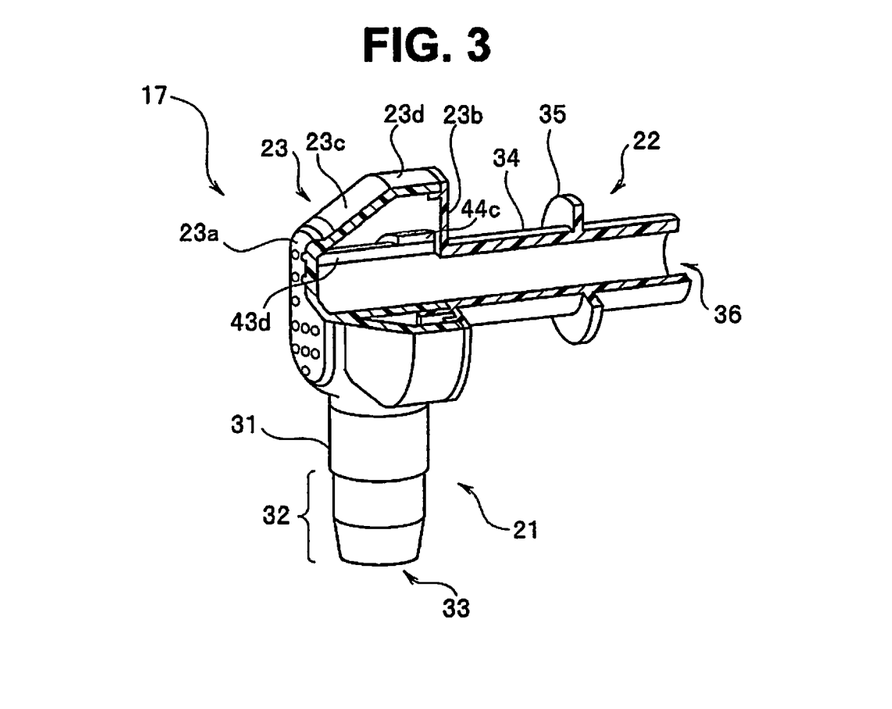
FIG. 3 is a partial cross-sectional view of the connection unit for air feeding tube according to the first embodiment of the present invention.

FIG. 2 is a perspective view of the connection unit 17 for air feeding tube. FIG. 3 is a partial cross-sectional view of the connection unit 17 for air feeding tube. The connection unit for air feeding tube (hereinafter, also called a connection unit) 17 includes a tube connection portion 21 to which the air feeding tube 13a is connected, an access port connection portion 22, and a coupling portion 23 that couples the tube connection portion 21 with the access port connection portion 22.

The tube connection portion 21 includes a tubular portion 31 that is a pipe, and at a distal end side portion of the tubular portion 31, a step portion 32 to which the air feeding tube 13a is attached is formed. When the distal end portion of the air feeding tube 13a is externally attached over the tubular portion 31, and is connected and fixed to the tube connection portion 21, carbon dioxide gas is introduced into the connection unit 17 through an opening 33 at the distal end of the tubular portion 31. In other words, the air feeding tube 13a is connectable to the tubular portion 31, and the tubular portion 31 includes, at the distal end portion, the opening 33 that is an inlet of gas from the air feeding tube 13a.

Figure 9:
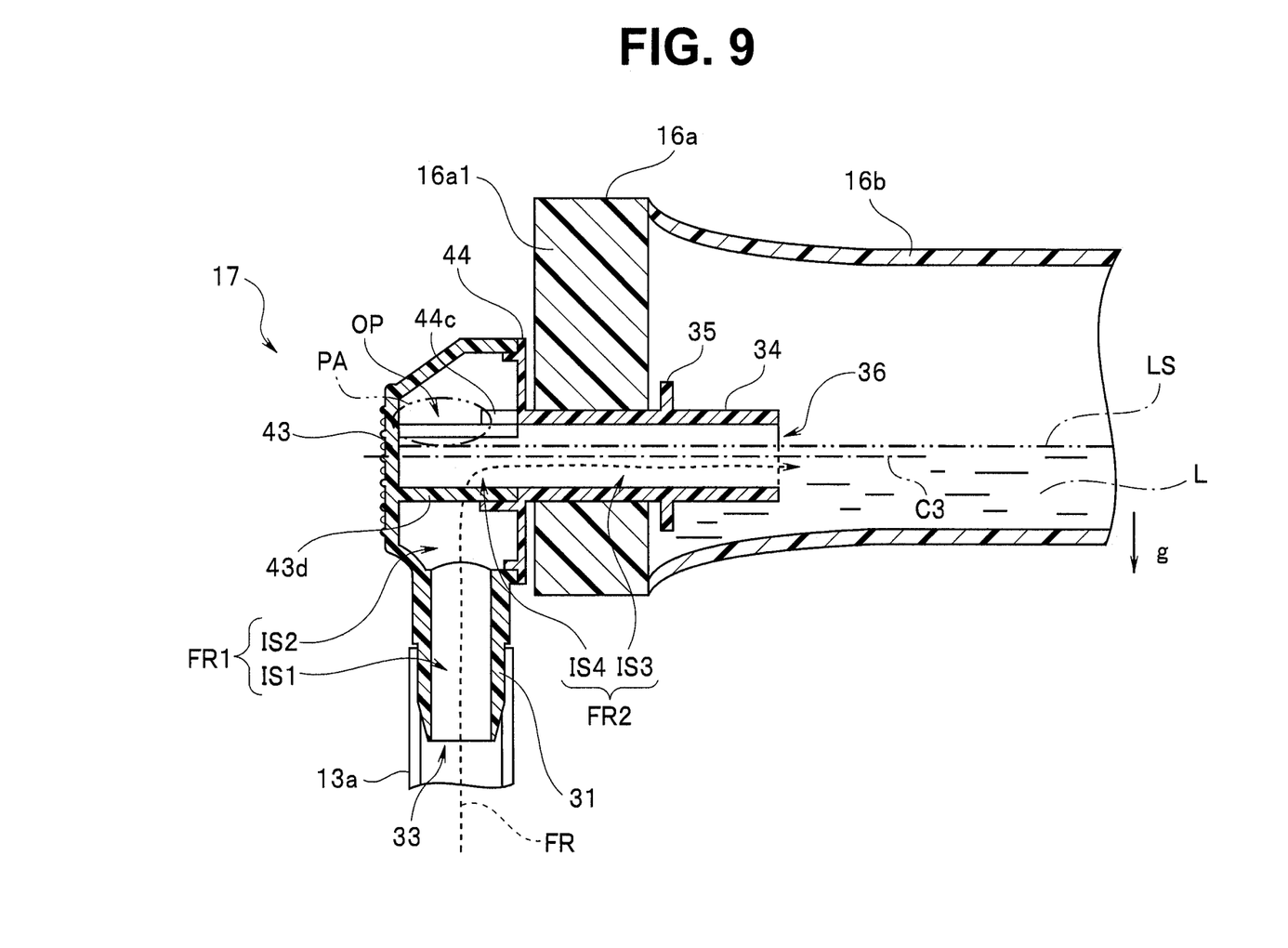
FIG. 9 is a sectional view showing a state where the connection unit for air feeding tube is attached to an access port according to the first embodiment of the present invention.

The access port connection portion 22 includes a tubular portion 34 that is a pipe, and is attached to the access surface portion of the access port 16 (described later) to be attached to the anus of the patient M. More specifically, as shown in FIG. 9, the access port connection portion 22 is attached to the access port 16 so as to be through the access surface portion of the seal cap 16a of the access port 16. The access port connection portion 22 includes an outward flange 35 at an intermediate portion of the tubular portion 34. The outward flange 35 constitutes an anti-falling portion that prevents the connection unit 17 from falling out of the access surface portion of the seal cap 16a.

When the connection unit 17 is attached to the access port 16 described later, an opening 36 at the distal end of the tubular portion 34 is arranged in the access port 16. In other words, carbon dioxide gas passes through a predetermined flow path in the connection unit 17, and is discharged out of the opening 36 that is an outlet of the tubular portion 34. In other words, the tubular portion 34 is connectable to the access port 16, and includes, at the distal end portion, the opening 36 that is an outlet of gas from the air feeding tube 13a.

The coupling portion 23 has an appearance shape of a substantially cylindrical shape. For more detail, the coupling portion 23 has an oval cylindrical shape. The oval is a shape like a track in an athletics stadium. The oval has an oval cylindrical shape extending in a direction of a longitudinal axis C1. The coupling portion 23 couples the tubular portion 31 with the tubular portion 34.

Furthermore, as shown in FIG. 2, one surface 23a of two surfaces 23a and 23b of the substantially cylindrical shaped coupling portion 23 are chamfered along the edge of the oval. As a result, the coupling portion 23 has a truncated-cone-shaped portion 23c. The tube connection portion 21 extends from a side surface 23d of the cylindrical shaped coupling portion 23, parallel to the longitudinal axis C1.

The access port connection portion 22 extends from the surface 23b on the opposite side of the surface 23a of the coupling portion 23 in a direction orthogonal to a central axis C2 of the tube connection portion 21. In other words, the central axis C2 of the tube connection portion 21 is parallel to the longitudinal axis C1 of the oval coupling portion 23, and a central axis C3 of the access port connection portion 22 is orthogonal to the central axis C2.

Since in TaTME, the access port connection portion 22 is inserted into the anus of the patient M lying on the bed 15 in the supine position, the central axis C3 of the access port connection portion 22 is substantially parallel to the horizontal direction. The central axis C2 of the tube connection portion 21, to which the distal end portion of the air feeding tube 13a is connected, is substantially parallel to the vertical direction owing to the weight of the air feeding tube 13a.

Figure 4:
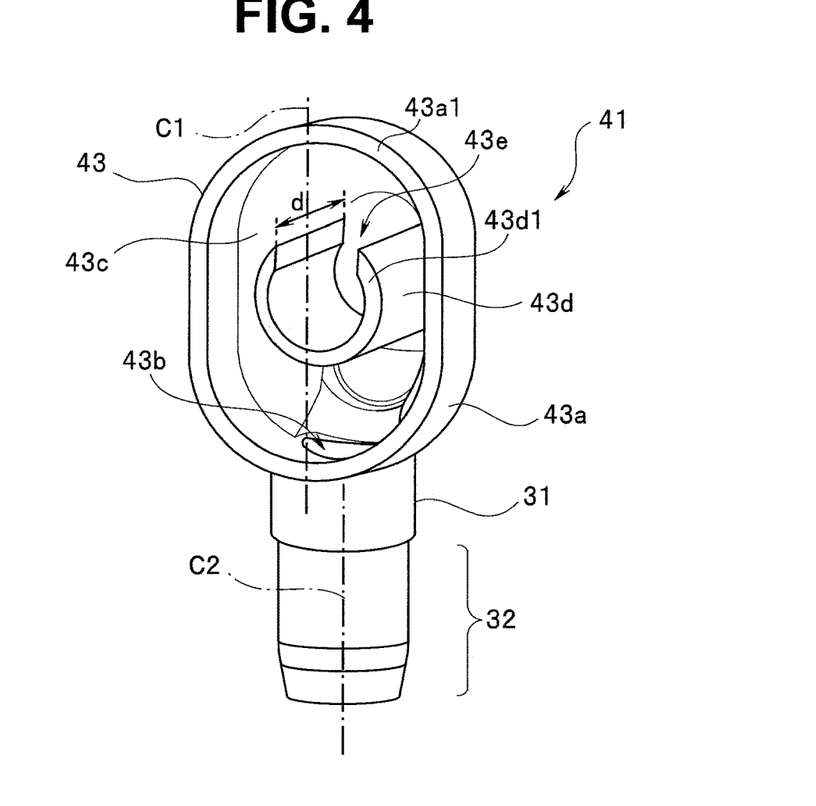
FIG. 4 is a perspective view of a cover member included in the connection unit for air feeding tube according to the first embodiment of the present invention.
Figure 5:
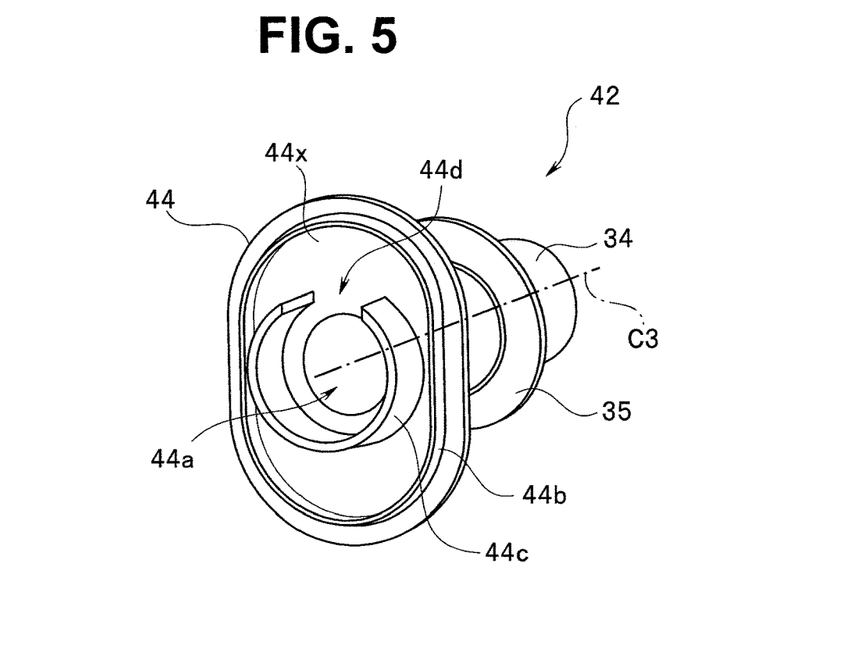
FIG. 5 is a perspective view of a cap member included in the connection unit for air feeding tube according to the first embodiment of the present invention.
Figure 6:
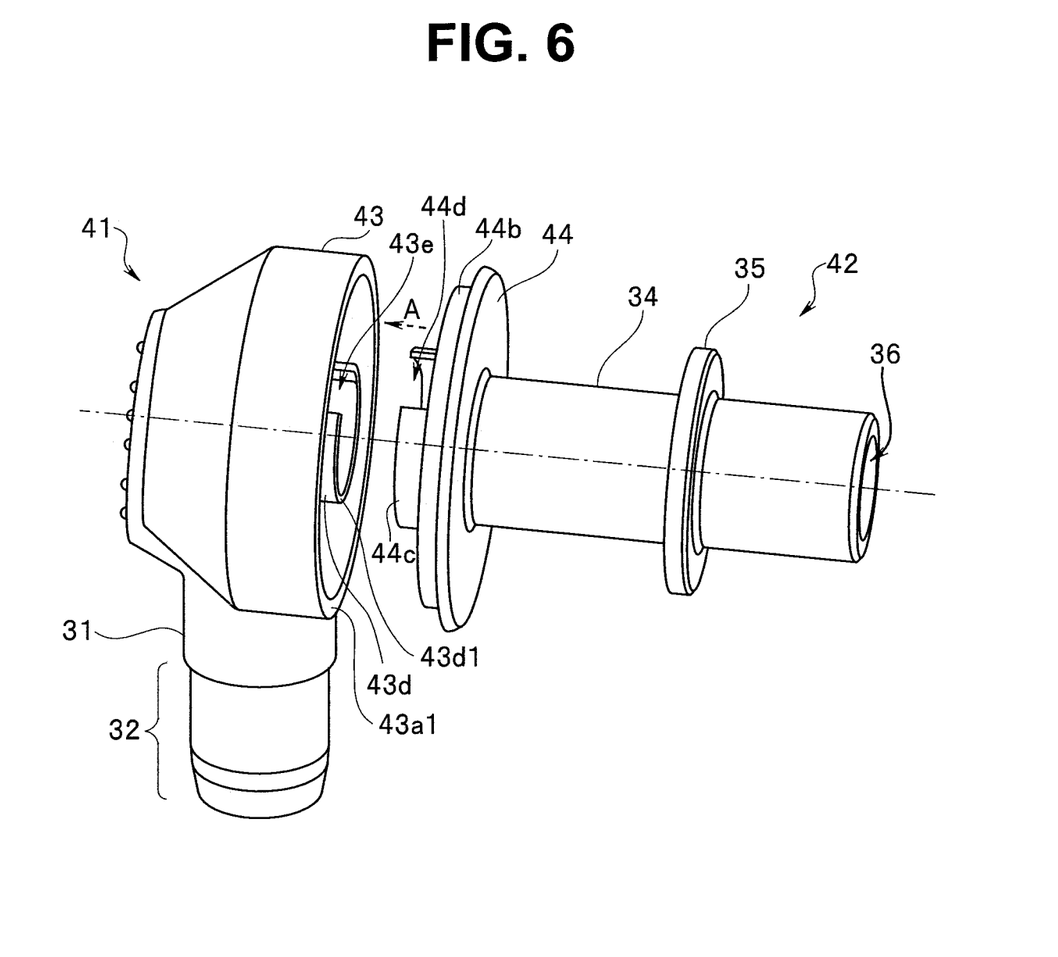
FIG. 6 is an exploded view of the connection unit for air feeding tube according to the first embodiment of the present invention.

FIG. 4 is a perspective view of a cover member 41 included in the connection unit 17. FIG. 5 is a perspective view of a cap member 42 included in the connection unit 17. FIG. 6 is an exploded view of the connection unit 17.

The connection unit 17 includes two members that are the cover member 41 and the cap member 42. Both of the cover member 41 and the cap member 42 are made of resin. As shown in FIG. 4, the cover member 41 includes a bottomed-cylindrical portion 43 having a sectional shape of an oval. The tube connection portion 21 is formed so as to protrude from an outer peripheral surface of a thin-walled portion 43a of the cover member 41, parallel to the longitudinal axis C1. Consequently, an opening 43b that communicates with an inner space of the tube connection portion 21 is formed on an inner peripheral surface of the thin-walled portion 43a of the cover member 41.

On a bottom surface 43c of the cover member 41, a partial cylindrical portion 43d is formed so as to protrude by a protruding amount d in a direction orthogonal to the central axis C2. As shown in FIG. 4, the central axis of the partial cylindrical portion 43d is orthogonal to the central axis C2 of the tube connection portion 21, and at the partial cylindrical portion 43d, a penetration slit 43e extending in a direction orthogonal to the central axis C2 is formed. The protruding amount d of the partial cylindrical portion 43d is an amount that brings a distal end surface 43d1 of the partial cylindrical portion 43d in close contact with the cap member 42 when the cap member 42 is attached to the cover member 41.

As shown in FIG. 5, the cap member 42 has an oval plate-shaped portion 44. The access port connection portion 22 is formed so as to protrude from the plate-shaped portion 44 in a direction orthogonal to the longitudinal axis C1. In the plate-shaped portion 44, an opening 44a communicating with an inner space of the access port connection portion 22 is formed. The plate-shaped portion 44 has an oval-shaped protruding portion 44b in close contact with the distal end portion of the inner peripheral surface of the thin-walled portion 43a of the cover member 41.

Furthermore, the cap member 42 is formed on one surface 44x of the plate-shaped portion 44 so as to encircle the opening 44a, and includes a partial cylindrical portion 44c formed so as to protrude in an opposite direction of the direction in which the access port connection portion 22 protrudes. The central axis of the partial cylindrical portion 44c is parallel to the central axis C3 of the access port connection portion 22, and a penetration slit 44d parallel to the central axis C3 is formed in the partial cylindrical portion 44c.

As shown in FIG. 6, the cap member 42 is bonded to the cover member 41 with an adhesive. Specifically, the adhesive is applied on a distal end surface 43a1 of the thin-walled portion 43a and the distal end surface 43d1 of the partial cylindrical portion 43d, and as indicated by a broken line arrow A, the cap member 42 is fixed to the cover member 41 so as to fit the protruding portion 44b of the cap member 42 into the inner peripheral surface of the thin-walled portion 43a of the cover member 41. At this time, the distal end surface 43d1 is in close contact with the plate-shaped portion 44. As described above, the connection unit 17 includes the cover member 41 and the cap member 42.

Figure 7:
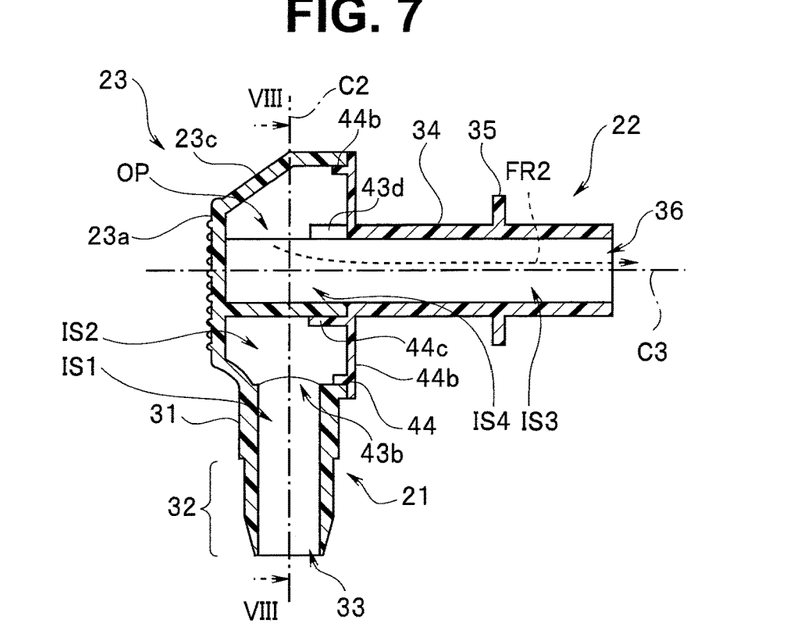
FIG. 7 is a sectional view of the connection unit for air feeding tube taken along a plane including a central axis of a tube connection portion and a central axis of an access port connection portion according to the first embodiment of the present invention.
Figure 8:
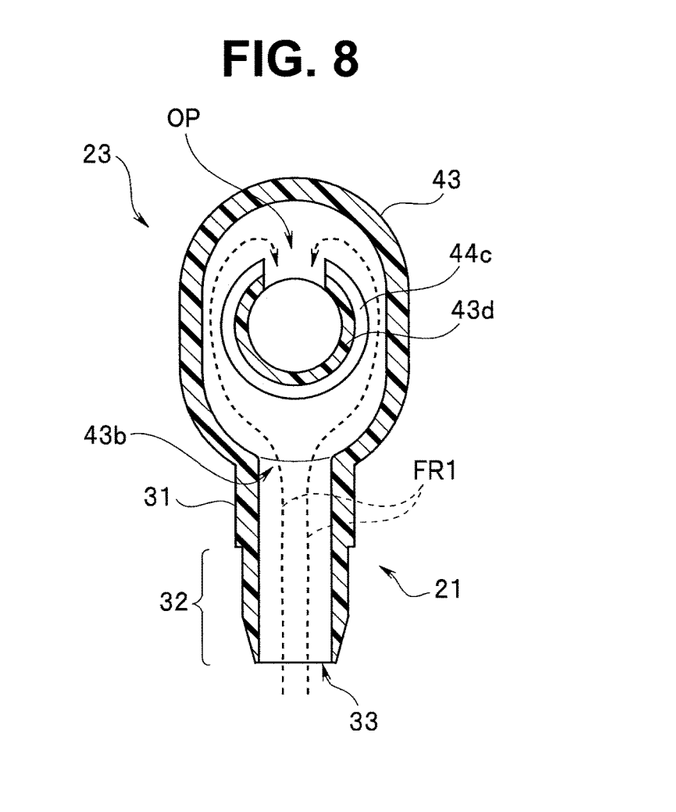
FIG. 8 is a sectional view of the connection unit for air feeding tube viewed from the cover member in a direction of the central axis of the access port connection portion taken along line VIII-VIII of FIG. 7.

FIG. 7 is a sectional view of the connection unit 17 for air feeding tube taken along a plane including the central axis C2 of the tube connection portion 21 and the central axis C3 of the access port connection portion 22. FIG. 8 is a sectional view of the connection unit 17 for air feeding tube viewed from the cover member 41 in a direction of the central axis C3 of the access port connection portion 22 taken along line VIII-VIII of FIG. 7.

An inner space IS1 of the tube connection portion 21, and an internal space IS2 of the coupling portion 23 constitute a first flow path FR1 through which gas from the air feeding tube 13a passes. The first flow path FR1 is a flow path formed from the opening 33 toward the inside of the coupling portion 23. The internal space IS2 of the coupling portion 23 is a space formed of the inner wall of the cover member 41, the one surface 44x of the cap member 42, and outer peripheral surfaces of the partial cylindrical portions 43d and 44c.

An inner space IS3 of the access port connection portion 22, and an internal space IS4 including the inside of the partial cylindrical portion 43d of the coupling portion 23 constitute a second flow path FR2 through which gas from the air feeding tube 13a passes. The second flow path FR2 is a flow path formed from the inside of the coupling portion 23 toward the opening 36. The flow path FR1 communicates with the flow path FR2 through an opening OP in the coupling portion 23. The opening OP is formed of the penetration slits 43e and 44d. The opening OP is positioned on the opposite side of the opening 33 of the tube connection portion 21 with respect to the central axis C3.

The gas having flown from the air feeding tube 13a into the opening 33, first, flows into the inner space IS1 in the connection unit 17. The gas having flown into the inner space IS1 flows into the communicating internal space IS2. The gas having flown into the internal space IS2 passes through the opening OP and flows into the internal space IS4 of the partial cylindrical portion 43d. The gas having flown into the internal space IS4 flows out of the opening 36 through the inner space IS3 of the access port connection portion 22.

Thus, the gas having flown from the air feeding tube 13a into the opening 33 flows into the first flow path FR1 in the connection unit 17, flows into the second flow path FR2 through the opening OP, and flows out of the opening 36. In other words, in the connection unit 17, an air feeding flow path FR through which gas is fed is formed so as to include the opening 33 and the opening 36. Thus, the air feeding flow path FR for gas from the insufflation device 13 into the rectum is formed of the first flow path FR1 and the second flow path FR2.

As described above, the first flow path FR1 is formed of the inner space IS1 of the tubular portion 31 and the internal space IS2 in the coupling portion 23, and the second flow path FR2 is formed of the inner space IS3 of the tubular portion 34 and the internal space IS4 in the coupling portion 23. A part of the air feeding flow path FR for gas is provided between the internal space IS2 and the internal space IS4 in the coupling portion 23, and includes the opening OP formed on the opposite side of the opening 33 with respect to the central axis C3 of the tubular portion 34.

(Operation)

Next, the operation of the connection unit 17 is described.

FIG. 9 is a sectional view showing a state where the connection unit 17 is attached to the access port 16. FIG. 9 shows a section of the connection unit 17 taken along the central axes C2 and C3.

As described above, the access port 16 includes the seal cap 16a, and the access port connection portion 22 is attached so as to be through the seal cap 16a. More specifically, the connection unit 17 is attached to the access surface portion 16a1 of the seal cap 16a such that the outward flange 35 is positioned in the access channel portion 16b through the seal cap 16a.

The connection unit 17 is attached to the access port 16 such that the opening 33 is positioned downward in the gravitational direction g. Gas, such as carbon dioxide gas, from the air feeding tube 13a flows into the tubular portion 31 through the opening 33. The gas having flown into the tubular portion 31 flows into the coupling portion 23 along the flow path FR1.

The gas having flown into the coupling portion 23 passes through the opening OP, flows into the inner space IS3 of the access port connection portion 22 along the flow path FR2, and flows out of the opening 36. Specifically, when the air feeding tube 13a is fixed to the connection unit 17 for air feeding tube, a part of the air feeding flow path for the gas is formed so as to pass through a certain area PA, in which the opening OP resides, on the opposite side of the opening 33 with respect to the central axis C3 of the tubular portion 34. In other words, when the air feeding tube 13a is fixed to the connection unit 17 for air feeding tube and is used, a part of the air feeding flow path FR for the gas is formed so as to pass through the area PA located at a position opposite to the gravitational direction g with respect to the central axis C3 of the tubular portion 34.

During TaTME, the surgeon inserts a rigid endoscope and a treatment instrument into the rectum through the access port 16, and performs a treatment. By the treatment, liquid, such as blood and normal saline, is accumulated in the rectum.

As shown in FIG. 9, liquid L is accumulated in the access port 16, and enters the inside of the inner space IS3 of the tubular portion 34 and the internal space IS4 of the partial cylindrical portion 43d through the opening 36 in a case where the amount of the liquid increases.

The liquid L in the access port 16 is sucked through the suction tube 14a, but as the amount of the liquid L increases, a liquid surface LS of the liquid L rises in an opposite direction of the gravitational direction g, as shown in FIG. 9.

However, since the opening OP is positioned in the opposite direction of the gravitational direction g with respect to the liquid surface LS of the liquid L, the liquid in the flow path FR2 hardly enters the internal space IS2 through the opening OP. In other words, until the height of the liquid surface LS of the liquid L exceeds the height of the opening OP located at a position opposite to the gravitational direction g, the liquid does not enter the internal space IS2. In other words, until the liquid surface LS of the liquid L exceeds an upper end portion of the opening 36, the liquid does not enter the internal space IS2 of the coupling portion 23.

If a conventional trocar is used, the liquid accumulated in the rectum easily enters the inside of the air feeding tube 13a. In a case where the liquid enters the inside of the air feeding tube, air feeding from the insufflation device 13 becomes unstable, and there is a possibility that the pressure in the rectum cannot be maintained to a desired pressure.

For example, the insufflation device 13 constantly monitors the pressure in the rectum through the pressure measurement tube 13b in order to maintain the pressure in the rectum constant. Suction is constantly performed for discharging smoke. The insufflation device 13 reduces the air feeding flow rate when the pressure in the rectum is higher than a setting value, and increases the air feeding flow rate when the pressure in the rectum is lower than the setting value.

For example, the pressure in the rectum is measured through the pressure measurement tube 13b, and the pressure in the rectum is calculated and estimated on the basis of the flow rate and the pipeline resistance of the air feeding tube 13a. The insufflation device 13 detects clogging and falling of the air feeding tube 13a by determining whether the calculated estimated pressure coincides with the measured pressure.

However, if the liquid enters the inside of the air feeding tube 13a, the pipeline resistance is changed, and the insufflation device 13 cannot correctly estimate the air feeding flow rate. As a result, the insufflation device 13 cannot appropriately control the air feeding rate based on the difference between the estimated pressure and the measured pressure, and for example, if air feeding at an appropriate rate is stopped, an appropriate surgical visual field and operation space cannot be appropriately secured.

On the contrary, through use of the connection unit for air feeding tube according to the embodiment described above, no liquid enters the inside of the air feeding tube 13a, and resultantly, the insufflation device 13 can appropriately continue the control of the air feeding rate.

As described above, according to the embodiment described above, the connection unit for air feeding tube and the method of feeding air into the connection unit for air feeding tube which hardly allow the liquid to enter the inside of the air feeding tube can be provided.

Second Embodiment

Figure 10:
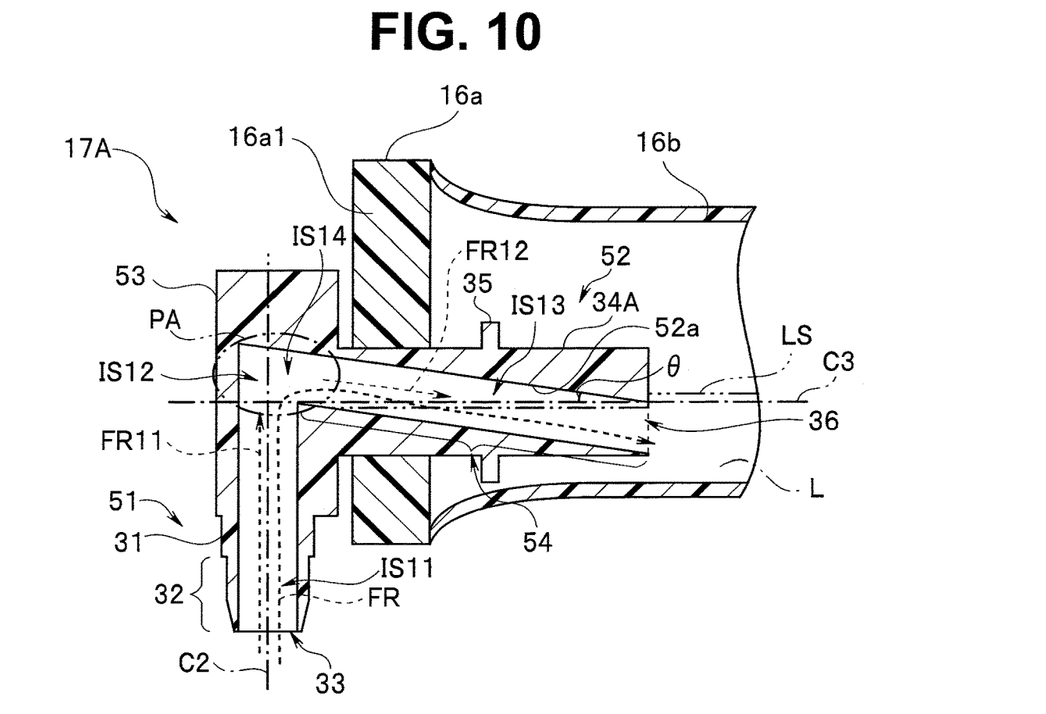
FIG. 10 is a sectional view showing a state where a connection unit for air feeding tube is attached to an access port according to a second embodiment of the present invention.
Figure 11:
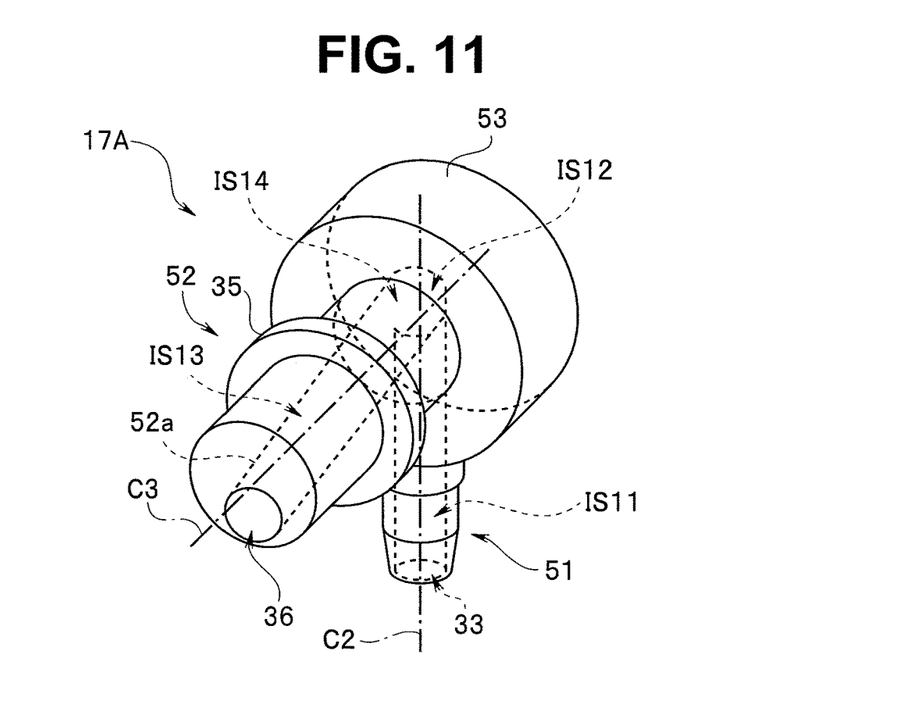
FIG. 11 is a perspective view of the connection unit according to the second embodiment of the present invention.

According to the first embodiment, the opening OP is provided between the internal spaces IS2 and IS4 in the coupling portion 23, and the opening OP is formed on the opposite side of the opening 33 with respect to the central axis C3 of the tubular portion 34. Accordingly, a part of the air feeding flow path FR for the gas from the insufflation device 13 is formed so as to pass through the area PA on the opposite side of the opening 33 with respect to the central axis C3 of the tubular portion 34. On the other hand, according to a second embodiment, a part of an inner flow path of a tubular portion 34A is formed to be inclined from the central axis C3 of the tubular portion 34A. Accordingly, the part of the air feeding flow path FR for the gas from the insufflation device 13 is formed so as to pass through the area PA on the opposite side of the opening 33 with respect to the central axis C3 of the tubular portion 34A.

In the embodiment, the same components as those of the first embodiment are assigned the same symbols, and the description is omitted.

FIG. 10 is a sectional view showing a state where a connection unit 17A for air feeding tube is attached to an access port 16 according to the embodiment. FIG. 10 shows a section of the connection unit 17A taken along the central axes C2 and C3. FIG. 1l is a perspective view of the connection unit 17A.

The connection unit 17A includes a tube connection portion 51 to which the air feeding tube 13a is connected, an access port connection portion 52, and a coupling portion 53 that couples the tube connection portion 51 with the access port connection portion 52.

The tube connection portion 51 includes a tubular portion 31, and at a distal end side portion of the tubular portion 31, a step portion 32 to which the air feeding tube 13a is attached is formed. The distal end of the tubular portion 31 includes an opening 33. The coupling portion 53 includes an internal space IS12. An inner space IS11 of the tube connection portion 51, and the internal space IS12 of the coupling portion 53 constitute a first flow path FR11 through which gas from the air feeding tube 13a passes.

The access port connection portion 52 includes a tubular portion 34A that is a pipe, and is attached to the access surface portion of the access port 16 to be attached to the anus of the patient M. The distal end of the tubular portion 34A has an opening 36. The access port connection portion 52 includes an outward flange 35 at an intermediate portion of the tubular portion 34A.

The access port connection portion 52 has a cylindrical shape, and includes a pipeline 52a formed to be inclined by a predetermined angle θ from the central axis C3 so as to be apart from the opening 33 from the opening 36 toward the coupling portion 53. The pipeline 52a constitutes an inner space IS13 of the access port connection portion 52. The coupling portion 53 includes an internal space IS14 that communicates with the inner space IS13. The internal space IS12 communicates with the internal space IS14.

An area 54 of the inner space IS13 and the internal space IS14 is inclined by the predetermined angle θ from the central axis C3 so as to be apart from the opening 33 from the opening 36 toward the coupling portion 53. The inner space IS13 of the access port connection portion 52 and the internal space IS14 of the coupling portion 53 constitute a second flow path FR12 through which the gas from the air feeding tube 13a passes.

As described above, the second flow path FR12 is formed to be inclined from the central axis C3, and the part of the second flow path FR12 is thus formed so as to pass through the opposite side of the opening 33 with respect to the central axis C3 of the tubular portion 34A.

For example, the connection unit 17A can be fabricated as follows. The opening 33, the inner space IS11 and the internal space IS12 are formed by penetrating a member that is made of resin and has an appearance shape as shown in FIG. 11 in the direction of the central axis C2. Furthermore, the opening 36, the inner space IS13 and the internal space IS14 are formed so as to allow the internal spaces IS12 and IS14 to communicate with each other, by penetrating the member made of resin in a direction inclined by the predetermined angle θ from the central axis C3.

As shown in FIG. 10, when the connection unit 17A is attached to an access surface portion 16a1 of the seal cap 16a, gas, such as carbon dioxide gas, from the air feeding tube 13a flows into the tubular portion 31 through the opening 33. The gas having flown into the tubular portion 31 passes through the internal spaces IS12 and IS14 of the coupling portion 53 along the flow path FR11, flows into the inner space IS13 of the access port connection portion 52 along the flow path FR12, and flows out of the opening 36.

Even in a case where liquid, such as blood and normal saline, is accumulated in the rectum during TaTME, the part of the area 54 of the inner space IS13 and the internal space IS14, which is located away from the opening 36, is in the area on the opposite side of the opening 33 with respect to the central axis C3 of the tubular portion 34A. Therefore, the part of the air feeding flow path FR for gas from the insufflation device 13 passes through the area PA on the opposite side of the opening 33 with respect to the central axis C3 of the tubular portion 34A. The area PA on the opposite side of the opening 33 is the opposite side of the gravitational direction. In other words, the part of the flow path FR12 is formed so as to pass through the opposite side of the opening 33 with respect to the central axis C3 of the tubular portion 34A, and thus the part of the air feeding flow path FR for the gas is formed so as to pass through the area PA on the opposite side of the opening 33 with respect to the central axis C3 of the tubular portion 34A.

In other words, unless the liquid surface LS of the liquid L rises in a direction inclined by the predetermined angle θ from the central axis C3 and exceeds the area PA on the opposite side of the opening 33 with respect to the central axis C3 of the tubular portion 34A, the liquid L does not enter the inside of the inner space IS11 of the tube connection portion 51. Consequently, the liquid hardly enters the inside of the inner space IS11 of the tube connection portion 51 through the communicating portion.

Consequently, also according to the embodiment, the connection unit for air feeding tube and the method of feeding air into the connection unit for air feeding tube which hardly allow the liquid to enter the inside of the air feeding tube can be provided.

Third Embodiment

Figure 12:
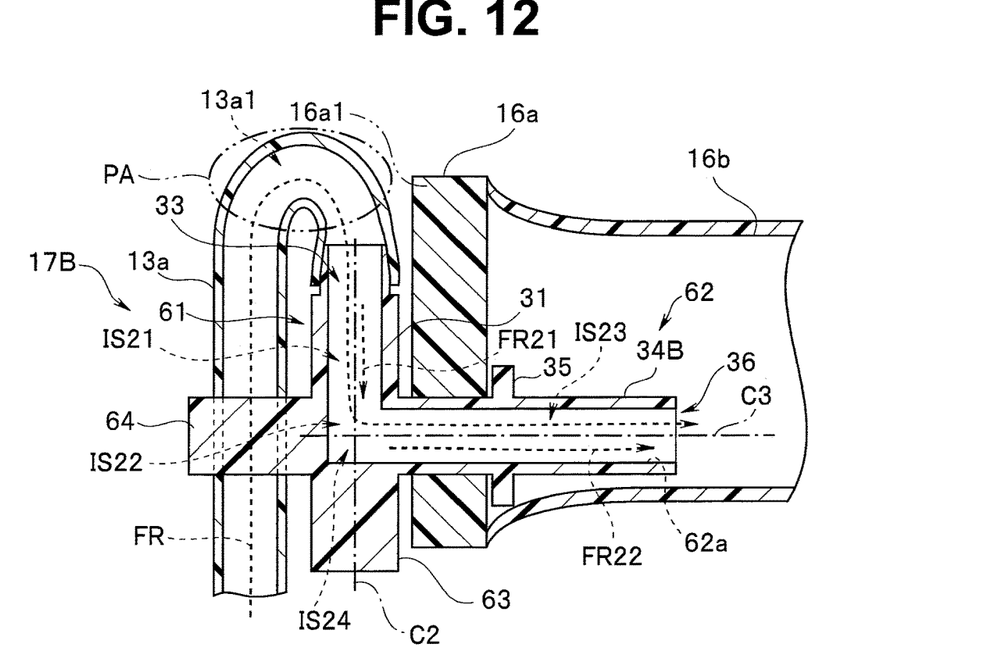
FIG. 12 is a sectional view showing a state where a connection unit for air feeding tube is attached to an access port according to a third embodiment of the present invention.
Figure 13:
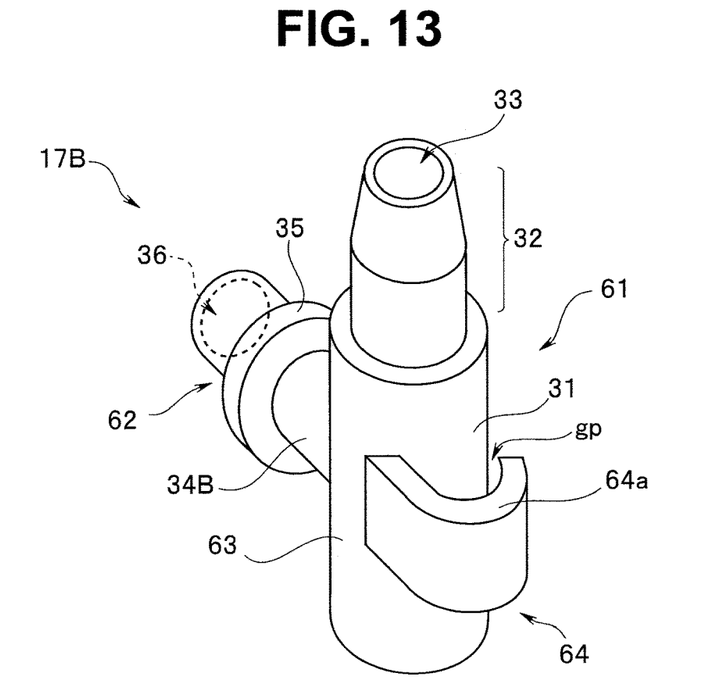
FIG. 13 is a perspective view of the connection unit for air feeding tube according to the third embodiment of the present invention.

In the first and second embodiments, the air feeding tube 13a is connected to the connection unit for air feeding tube from the below in the gravitational direction, but in a third embodiment, the air feeding tube 13a is connected to the connection unit for air feeding tube from the above in the gravitational direction, and is fixed to the connection unit so as to bend the air feeding tube 13a downward. Accordingly, the part of the air feeding flow path FR for the gas from the insufflation device 13 is formed so as to pass through the area PA located at the position opposite to the gravitational direction with respect to the central axis C3 of a tubular portion 34B.

In the embodiment, the same components as those of the first embodiment are assigned the same symbols, and the description is omitted.

FIG. 12 is a sectional view showing a state where a connection unit 17B for air feeding tube is attached to an access port 16 according to the embodiment. FIG. 12 shows a section of the connection unit 17B taken along the central axes C2 and C3. FIG. 13 is a perspective view of the connection unit 17B.

The connection unit 17B includes a tube connection portion 61 to which the air feeding tube 13a is connected, an access port connection portion 62, and a coupling portion 63 that couples the tube connection portion 61 with the access port connection portion 62.

As shown in FIG. 13, the tube connection portion 61 includes a tubular portion 31, and at a distal end side portion of the tubular portion 31, a step portion 32 to which the air feeding tube 13a is attached is formed. The distal end of the tubular portion 31 includes an opening 33. The coupling portion 63 includes an internal space IS22. An inner space IS21 of the tube connection portion 61 constitutes a first flow path FR21 through which gas from the air feeding tube 13a passes. In other words, the first flow path FR21 is formed from the opening 33 toward the inside of the coupling portion 63.

The access port connection portion 62 includes a tubular portion 34B that is a pipe, and is attached to the access surface portion of the access port 16 to be attached to the anus of the patient M. The distal end of the tubular portion 34B has an opening 36. The access port connection portion 62 includes an outward flange 35 at an intermediate portion of the tubular portion 34B.

The access port connection portion 62 has a cylindrical shape, and includes a pipeline 62a formed parallel to the central axis C3. The pipeline 62a constitutes an inner space IS23 of the access port connection portion 62. The coupling portion 63 includes an internal space IS24 that communicates with the inner space IS23. The inner space IS23 communicates with the internal space IS24. The inner space IS23 of the access port connection portion 62 and the internal space IS24 of the coupling portion 63 constitute a second flow path FR22 through which the gas from the air feeding tube 13a passes. In other words, the second flow path FR22 is formed from the inside of the coupling portion 63 toward the opening 36.

The coupling portion 63 includes a holding portion 64 for fixing and holding the air feeding tube 13a. In view in the central axis C2 direction, the holding portion 64 includes a hook portion 64a that protrudes from the outer peripheral portion to form a hook shape. In order to allow the air feeding tube 13a to pass through the inside of the hook portion 64a and be stored, the holding portion 64 has a gap gp between a distal end portion of the hook portion 64a and an outer peripheral surface of the holding portion 64, and has a curved shape. The hook portion 64a engages with the air feeding tube 13a.

The holding portion 64 protrudes along the central axis C3 on the opposite side of the access port connection portion 62 with respect to the central axis C2 of the tube connection portion 61. The air feeding tube 13a is connected to the tube connection portion 61.

As shown in FIG. 12, the air feeding tube 13a extending in one direction of the central axis C2 from the tube connection portion 61 extends along the central axis C2, subsequently is bent in an opposite direction of the extending direction, and allows the middle of the air feeding tube 13a to be held by the holding portion 64. In other words, the air feeding tube 13a is bent by 180 degrees at the curved portion and is allowed to extend in the gravitational direction. Since the flexibility of the air feeding tube 13a causes a force of returning the air feeding tube 13a in an external radial direction of the central axis C2 in the holding portion 64, the air feeding tube 13a is caused to engage with the holding portion 64.

As shown in FIG. 12, when the connection unit 17B is attached to the access surface portion 16al of the seal cap 16a, gas, such as carbon dioxide gas, from the air feeding tube 13a flows into the tubular portion 31 through the opening 33. The gas having flown into the tubular portion 31 passes through the internal spaces IS22 and IS24 of the coupling portion 63 along the flow path FR21, flows into the inner space IS23 of the access port connection portion 62 along the flow path FR22, and flows out of the opening 36.

Even in the case where liquid, such as blood and normal saline, is accumulated in the rectum during TaTME, the curved portion of the air feeding tube 13a is in the area PA located at the position opposite to the gravitational direction with respect to the opening 36, and thus the part of the air feeding flow path FR for gas from the insufflation device 13 passes through the area PA located at the position opposite to the gravitational direction with respect to the central axis C3 of the tubular portion 34B. In other words, the part of the air feeding flow path FR for the gas is a part of the inner space 13al of the air feeding tube 13a when the air feeding tube 13a is fixed to the connection unit 17B for air feeding tube.

Unless the liquid surface LS of the liquid L in the access port 16 rises in a direction orthogonal to the central axis C3 and exceeds the area PA located at the position opposite to the gravitational direction with respect to the central axis C3 of the tubular portion 34B, the liquid L does not enter farther than the area PA of the air feeding tube 13a. Consequently, the liquid hardly enters the inside of the air feeding tube 13a.

Consequently, also according to the embodiment, the connection unit for air feeding tube and the method of feeding air into the connection unit for air feeding tube which hardly allow the liquid to enter the inside of the air feeding tube can be provided.

The present invention is not limited to the embodiments described above, and can be variously changed or modified in a range not departing from the gist of the present invention.

What is claimed is:

1. A connection unit for use with a gas feeding tube, the connection unit comprising:
   a first pipe including a first opening through which a gas from the gas feeding tube flows into the first pipe;
   a second pipe including a second opening through which the gas flows out from the second pipe;
   a coupling portion coupling the first pipe with the second pipe, the coupling portion having a blocking surface extending along a central axis direction of the second pipe, and
   a gas feeding flow path from the first opening to the second opening through which the gas is fed,
   wherein when the first pipe is configured to be fixed to the gas feeding tube, a part of the gas feeding flow path is configured such that the gas from the first pipe flows towards the blocking surface to block the gas from entering into the second pipe from a first side of the blocking surface that opposes the first opening, the blocking surface having a third opening on a second side opposing the first side across the central axis of the second pipe, the gas flowing into the second pipe from the third opening.

2. The connection unit according to claim 1, wherein the gas feeding flow path comprises:
   a first flow path formed from the first opening toward an inside of the coupling portion; and
   a second flow path formed from the inside of the coupling portion toward the second opening.

3. The connection unit according to claim 2, wherein the first flow path includes a first inner space of the first pipe and a first internal space in the coupling portion, the second flow path includes a second inner space of the second pipe, and a second internal space in the coupling portion, and the part of the gas feeding flow path for the gas is provided between the first internal space and the second internal space in the coupling portion.

4. The connection unit according to claim 2, wherein a portion of the second flow path is on an opposite side of the first opening with respect to the central axis of the second pipe.

5. The connection unit according to claim 1, wherein the coupling portion includes a cylindrical portion, the cylindrical portion extends from a proximal end of the second pipe.

6. The connection unit according to claim 5, wherein the third opening is located on a opposite side of the first opening.

7. The connection unit according to claim 6, wherein the central axis of the second pipe is orthogonal to a central axis of the first pipe.

8. The connection unit according to claim 1, wherein the central axis of the second pipe is orthogonal to a central axis of the first pipe.

9. The connection unit according to claim 1, wherein the second pipe is configured to be arrangeable substantially parallel to a surface of a bed used in an examination.

10. The connection unit according to claim 1, wherein the second pipe has a first portion and a second portion, a diameter of the second portion is smaller than a diameter of the first portion.

11. The connection unit according to claim 1, wherein the second pipe has a flange having an outer diameter larger than an outer diameter of the second pipe, the flange is located on an outer surface of the second pipe.

12. The connection unit according to claim 1, wherein the blocking surface extends entirely across an inside of the coupling portion.

13. A connection unit comprising:
a first pipe configured to be attached to a gas feeding tube;
a second pipe; and
a coupling portion forming an internal space, the coupling portion coupling the first pipe with the second pipe,
wherein the first pipe and a first portion of the coupling portion defining a first gas flow path from an inlet at the first pipe to the first portion of the coupling portion;
the second pipe and a second portion of the coupling portion defining a second gas flow path from the second portion of the coupling portion to an outlet at the second pipe;
the first portion of the coupling portion including a blocking surface extending entirely across an inside of the coupling portion,
the second portion of the coupling portion includes an opening through which the first gas flow path and the second gas flow path communicate; and
the opening entirely opposing the blocking surface across a central axis of the second pipe.

14. The connection unit according to claim 13, wherein the blocking surface extending toward along a center axis direction of the second pipe.

15. The connection unit according to claim 14, wherein the blocking surface comprises a cylindrical portion disposed in the coupling portion, the cylindrical portion being convex relative to the central axis of the second pipe.

16. The connection unit according to claim 13, wherein the opening is a first opening, the first pipe comprising a second opening through which the gas flows into the first pipe, the blocking surface opposing the second opening such that the gas from the first pipe flows towards the blocking surface to block the gas from entering into the second pipe from the first portion of the coupling portion.

* * * * *